United States Patent [19]

Payne

[11] 4,025,634

[45] May 24, 1977

[54] N-(ARYLSULFONYL)-ALPHA-NITRO-DELTA $^{2,alpha}$-PIPERIDINEACETAMIDES

[75] Inventor: George Bernson Payne, Modesto, Calif.

[73] Assignee: Shell Oil Company, Houston, Tex.

[22] Filed: Mar. 1, 1976

[21] Appl. No.: 662,627

[52] U.S. Cl. .......................... 424/267; 260/293.73
[51] Int. Cl.$^2$ ................. C07D 211/70; A01N 9/16
[58] Field of Search ............... 260/293.73; 424/267

[56] References Cited

FOREIGN PATENTS OR APPLICATIONS 2,321,523  11/1973  Germany

*Primary Examiner*—Norma S. Milestone

[57] ABSTRACT

Novel compounds, identified in the title, useful as insecticides.

4 Claims, No Drawings

N-(ARYLSULFONYL)-ALPHA-NITRO-DELTA $^{2,alpha}$-PIPERIDINEACETAMIDES

DESCRIPTION OF THE INVENTION

It has been found that useful insecticidal activity is possessed by N-(arylsulfonyl)-alpha-nitro-delta$^{2,alpha}$-piperideneacetamides.

These compounds are described by the formula:

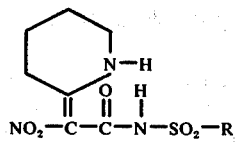

(I)

wherein R is phenyl or phenyl substituted by from one to two of one of halogen, nitro, cyano, alkyl or alkoxy of from one to six carbon atoms or phenoxy. Preferably, the halogen on the phenyl ring is middle halogen — i.e., chlorine or bromine.

For illustration, preparation of a typical species of the genus is described in the example included hereinafter. Other typical, illustrative species of this genus include those wherein the symbols represent the following moieties, this manner of naming these species being accurate, yet pointing out the differences between the different species more clearly than if the entire, complicated name of each species were to be given:

R = 4-chlorophenyl
2-fluorophenyl
phenyl
3-methylphenyl
4-bromophenyl
2-chlorophenyl
3-chlorophenyl
4-fluorophenyl
4-cyanophenyl
2,5-dichlorophenyl
2,5-dimethylphenyl
2-ethoxyphenyl
4-ethoxyphenyl
3-methoxyphenyl
4-methoxyphenyl
2-nitrophenyl
3-nitrophenyl
4-nitrophenyl
2-methylphenyl
4-methylphenyl
3-phenoxyphenyl
3,4-dichlorophenyl Compounds of this invention can be prepared by treating 2-(nitromethylene)-piperidine with an equimolar quantity of the appropriate arylsulfonyl isocyanate. Suitably, the piperidine is in solution in a solvent, such as an aromatic hydrocarbon, and the treatment is conducted at a temperature of from about 15° to about 40° C. The desired product, in each case, can be isolated from the crude reaction mixture and purified by conventional methos, such as filtration, extraction, crystallization and elution (chromatography). Preparation of the piperidine precursor is described in Example 1, hereinafter which also demonstrates the techniques for conducting the treatment, isolating and purifying the product.

The arylsulfonyl isocyanates as precursors asprecursors for compounds of this invention are a known class of compounds, as shown in the article by Henri Ulrich, "The Chemistry of Sulfonyl Isocyanates," Chemical Reviews, Vol. 65, pp. 369–376 (1965), and in U.S. Pat. Nos. 3,371,114 and 3,379,758.

A procedure for preparing compounds of this invention is illustrated in Example 1, following. The identity of the precursor had been, and the identity of the product was, confirmed by appropriate analyses.

EXAMPLE 1 alpha-nitro-N-(4-tolyl-sulfonyl)-delta-$^{2,alpha}$-piperidineacetamide (1)

To a solution of 100 g of delta-valerolactam in 300 ml of refluxing benzene, 126 g of dimethyl sulfate was added over 2.5 hours and refluxing was contained for 16 hours. The two-phase system was cooled with an ice bath and slowly treated with excess 50% aqueous $K_2CO_3$ solution. The organic phase was separated; the aqueous phase was extracted twice with benzene and the combined organic phase was dried ($MgSO_4$). Evaporation of the solvent under reduced pressure at room temperature followed by vacuum distillation gave 2-methoxy-3,4,5,6-tetrahydropyridine (1A) as a colorless liquid, b.p. 68°–71° (45Torr.).

A solution of 33.9 g of (1A) and 36.6 g of nitromethane was refluxed for 3 days, cooled and quenched in 1 liter of cold ether. Filtration gave a solid crude product, m.p. 79°–81°. Evaporation of the filtrate and trituration of the residue with cold ether give additional crude product. The crude product was continuously extracted from a Soxhlet thimble with ether for 18 hours, after which time only a small amount of dark oil remained. The solvent (now (not containing crystallized product) was cooled and the solid product was filtered, giving 2-(nitromethylene)piperidine (1B), as a pale yellow solid, m.p.: 80.5°–81°.

19.7 g of p-toluenesulfonylisocyanate was added to a solution of 14.2 g of 1B in 150 ml of dry benzene and the mixture was stirred overnight at room temperature. The mixture was filtered and the solid recrystallized from an acetone/pentane mixture to give 1, as a colorless solid, m.p.: 131°–133° (with decomposition).

Compounds of this invention are of particular interest for control of the larvae ("caterpillar" or "worm" forms) of insects of the genus Heliothis, such as H. zea (corn earworm, cotton bollworm, tomato fruitworm), H. virescens (tobacco budworm), houseflies and aphids. In tests that have been conducted Compound 1, a representative compound of the invention, has exhibited substantial activity with respect to larvae of the corn earworm, some activity with respect to houseflies, pea aphids and mosquito larvae, and no toxicity to the 2-spotted spider mite.

Activity of Compound 1 with respect to insects was determined by establishing the $LC_{50}$ dosage (in milligrams of test compound per 100 milliliters of solvent required in the solution of suspension of test compound used as a spray) to kill 50% of the test insects. The test insects were the housefly, corn earworm, pea aphid and 2-spotted spider mite. Activity with respect to mosquito larvae was determined by placing the larvae in water containing the test compound.

The invention includes within its scope insecticidal compositions comprising an adjuvant — that is, a carrier, optionally a surface-active agent — and, as active ingredient, at least one insecticide of this invention.

Likewise the invention includes also a method of combatting insect pests at a locus which comprises applying to the locus an effective amount of at least one insecticide of the invention.

The term "carrier" as used herein mean a material, which may be inorganic or organic and of synthetic or natural origin, with which the active compound is mixed or formulated to facilitate its application to the plant, seed, soil and other object to be treated, or its storage, transport or handling. The carrier may be a solid or a liquid.

Suitable solid carriers may be natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as for example, carbon and sulfur; natural and synthetic resins such as, for example, coumarone resins, polyvinyl chloride and styrene polymers and copolymers; solid polychlorophenols; bitumen, waxes such as beeswax, paraffin wax, and chlorinated mineral waxes; degradable organic solids, such as ground corn cobs and walnut shells; and solid fertilizers, for example, superphosphates.

Suitable liquid carriers include solvents for the compounds of this invention and liquids in which the toxicant is insoluble or only slightly soluble.

Examples of such solvents and liquid carriers generally are alcohols, for example, isopropyl alcohol, ketones, such as acetone, methyl ethyl ketone, methyl isobutyl ketone and cyclohexanone; ethers; aromatic hydrocarbons such as benzene, toluene and xylene; petroleum fractions such as kerosene, light mineral oils, chlorinated hydrocarbons, such as carbon tetrachloride, perchloroethylene, trichloroethane, including liquefied normally vaporous gaseous compounds. Mixtures of different liquids are often suitable.

If used, the surface-active agent may be an emulsifying agent or a dispersing agent or a wetting agent. It may be nonionic or ionic. Surface-active agents usually applied in formulating pesticides may be used. Examples of such surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; fatty acid salts of low molecular weight mono-, di- and trialkylamines; condensates of these with ethylene oxide and/or propylene oxide; condensation products of fatty alcohols or alkyl phenols for example, p-octylphenol or p-octylcresol, with ethylene oxide and/or propylene oxide; sulfates or sulfonates of these condensation products; alkali or alkaline earth metal salts, preferably sodium salts, of sulfuric or suflonic acids esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates or aerosols. Encapsulated formulations and controlled release formulations also are contemplated, as are bait formulations. Wettable powders are usually compounded to contain 25, 50 or 75%w of toxicant and usually contain, in addition to solid carrier, 3–10%w of a dispersing agent and, where necessary, up to 10%w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½–10%w of toxicant. Granules may be manufactured by agglomeration or impregnation techniques. Generally, granules will contain ½–25%w toxicant and 0–10%w of additives such as stabilizers, slow release modifiers and binding agents. Emulsifiable concentrates usually contain, in addition to the solvent, and when necessary, co-solvent, 10–50%w/v toxicant, 2–20%w/v emulsifiers and 0–20%w/v of appropriate additives such as stabilizers, penetrants and corrosion inhibitors. Suspension concentrates are compounded so as to obtain a stable, non-sedimenting, flowable product and usually contain 10–75%w toxicant, 0–5%w of dispersing agents, 0.1–10%w of suspending agents such as protective colloids and thixotropic agents, 0–10%w of appropriate additives such as defoamers, corrosion inhibitors, stabilizers, penetrants and stickers, and as carrier, water or an organic liquid in which the toxicant is substantially insoluble; certain organic additives or inorganic salts may be dissolved in the carrier to assist in preventing sedimentation or as antifreeze agents for water.

Aqueous dispersions and emulsions, for example, compositions obtained by diluting a wettable powder or an emulsifiable concentrate according to the invention with water, also lie within the scope of the present invention.

The compositions of the invention may also contain other ingredients, for example, other compounds possessing pesticidal, herbicidal or fungicidal properties, or attractants, such as pheromones, attractive food ingredients, and the like, for use in baits and trap formulations.

These compositions are applied in sufficient amount to supply the effective dosage of toxicant at the locus to be protected. This dosage is dependent upon many factors, including the carrier employed, the method and conditions of application, whether the formulation is present at the locus in the form of an aerosol, or as a film, or as discrete particles, the thickness of film or size of particles, the insect species to be controlled and the like, proper consideration and resolution of these factors to provide the necessary dosage of active material at the locus being within the skill of those versed in the art. In general, however, the effective dosage of toxicants of this invention at the locus to be protected — i.e. the dosage to which the insect contacts — is of the order of 0.001 to 0.5% based on the total weight of the formulation, though under some circumstances the effective concentration will be as little as 0.0001% or as much as 2%, on the same basis.

I claim:

1. A compound of the formula:

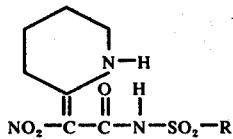

wherein R is phenyl or phenyl substituted by from one to two of one of halogen, nitro, cyano, alkyl or alkoxy of from one to six carbon atoms or phenoxy.

2. An insecticidal composition comprising a compound according to claim 1, together with an adjuvant therefor.

3. A method for controlling insects which comprises subjecting them to the action of a compound defined in claim 1.

4. A compound according to claim 1 wherein R is 4-methylphenyl.

* * * * *